(12) United States Patent
Pattanaik et al.

(10) Patent No.: US 12,046,340 B2
(45) Date of Patent: Jul. 23, 2024

(54) SYSTEM AND METHOD FOR FULFILLING PRESCRIPTIONS

(71) Applicant: Walmart Apollo, LLC, Bentonville, AR (US)

(72) Inventors: Samir Pattanaik, Bangalore (IN); Laxmi Swetha Guntakandla, Bangalore (IN); Bhaskar Mishra, San Mateo, CA (US)

(73) Assignee: Walmart Apollo, LLC, Bentonville, AR (US)

( * ) Notice: Subject to any disclaimer, the term of this patent is extended or adjusted under 35 U.S.C. 154(b) by 281 days.

(21) Appl. No.: 16/930,525

(22) Filed: Jul. 16, 2020

(65) Prior Publication Data

US 2021/0020287 A1 Jan. 21, 2021

Related U.S. Application Data

(60) Provisional application No. 62/898,076, filed on Sep. 10, 2019.

(30) Foreign Application Priority Data

Jul. 17, 2019 (IN) .............................. 201941028718

(51) Int. Cl.
*G16H 20/10* (2018.01)
*G06N 3/08* (2023.01)
(Continued)

(52) U.S. Cl.
CPC ............... *G16H 20/10* (2018.01); *G06N 3/08* (2013.01); *G06N 7/00* (2013.01); *G16H 30/00* (2018.01)

(58) Field of Classification Search
CPC .......... G16H 20/10; G16H 30/00; G06N 3/08; G06N 7/00
See application file for complete search history.

(56) References Cited

U.S. PATENT DOCUMENTS 5,597,995 A 1/1997 Williams
7,774,097 B2 8/2010 Rosenblum
(Continued)

FOREIGN PATENT DOCUMENTS

WO 2015130626 9/2015

OTHER PUBLICATIONS

US 8,560,343 B1, 10/2013, Tran (withdrawn)
(Continued)

*Primary Examiner* — Jonathan Ng
*Assistant Examiner* — Benjamin L. Hanks
(74) *Attorney, Agent, or Firm* — Foley IP Law, PLLC (57) ABSTRACT

A control circuit applies images obtained from the mobile electronic device to a trained model and responsively receiving prescription information. The prescription information indicates contents of the prescription, whether a prescription transfer is needed, and whether a prescription refill is needed. The control circuit determines an action based upon an analysis of the prescription information. The action is taken to electronically instruct a human or robot to fulfill the prescription. The action includes, when a prescription transfer is needed, transmitting an electronic message to a second pharmacy currently holding the medical prescription of the user.

15 Claims, 7 Drawing Sheets

(51) Int. Cl.
*G06N 7/00* (2023.01)
*G16H 30/00* (2018.01)

(56) References Cited

U.S. PATENT DOCUMENTS

| | | |
|---|---|---|
| 8,479,988 B2 | 7/2013 | Louie |
| 8,626,530 B1 | 1/2014 | Tran |
| 9,501,624 B2 | 11/2016 | Vishnubhatla |
| 10,074,076 B2 | 9/2018 | Weiss |
| D832,290 S | 10/2018 | Tran |
| 2013/0182295 A1 | 7/2013 | Naaman |
| 2014/0379371 A1* | 12/2014 | Tran .................. G16H 20/10 705/2 |
| 2015/0242592 A1* | 8/2015 | Weiss .................. G16H 10/60 705/2 |
| 2017/0011195 A1 | 1/2017 | Arshad |
| 2017/0039457 A1* | 2/2017 | Yu .................. G06N 3/02 |
| 2020/0126663 A1* | 4/2020 | Lucas .............. G06V 30/19013 |

OTHER PUBLICATIONS

Carezone; "An ecommerce platform for pharmacy"; https://carezone.com/platform; available at least as early as 2019; pp. 1-3.
Carezone; "Manage your health, without the headache."; https://carezone.com/home; available at least as early as 2019; pp. 1-3.
Rite Aid; "Rite Aid Mobile App"; https://www.riteaid.com/mobile-app; available at least as early as 2019; pp. 1-10.
Rite Aid; "RiteAid App—MyPharmacy"; https://youtu.be/hafQdFdeYcl, published on Feb. 7, 2019, pp. 1-3.

* cited by examiner

SYSTEM AND METHOD FOR FULFILLING PRESCRIPTIONS

CROSS REFERENCES TO RELATED APPLICATIONS

This application claims the benefit of Indian Provisional Application No. 201941028718, filed Jul. 17, 2019, and U.S. Provisional Application No. 62/898,076, filed Sep. 10, 2019, both of which are incorporated herein by reference in their entireties.

TECHNICAL FIELD

These teachings relate to fulfilling medical prescriptions.

BACKGROUND

Customers receive medical prescriptions for medications to treat various illnesses. These medical prescriptions sometimes are rendered in paper (e.g., a doctor writes a prescription on a paper form). More recently, many prescriptions are created and maintained in an electronic form. In any case, the prescription is sent to or presented to a pharmacy for fulfillment. In many cases, the patient goes to the pharmacy to collect the prescription. In other cases, the prescription may be mailed or shipped directly to the residence of the patient.

Various steps need to be performed by the patient in order to receive the prescription. In some cases, the customer or patient physically travels to the pharmacy. Once at the pharmacy, the patient typically must identify themselves and pay for the prescription. Sometimes, a patient (or medical personnel) seeks to transfer the prescription from one pharmacy to another. This can occur for many reasons (e.g., the patient moves, receives better prices at the new pharmacy, or simply prefers the new pharmacy). All of these steps lead to mistakes on entering information and delays in receiving prescriptions. These issues, in turn, lead to customer frustration with previous approaches.

BRIEF DESCRIPTION OF THE DRAWINGS

The above needs are at least partially met through the provision of approaches for fulfilling medical prescriptions, wherein.

DETAILED DESCRIPTION

Generally speaking, the present approaches use a mobile electronic device to scan images of prescription items including, for example, insurance cards, prescriptions, and/or retail store membership cards of customers. In aspects, a mathematical model such as a CNN network is trained to recognize prescription-related information in the images. The scanned images are applied to the model and, as a result, information (e.g., information concerning the contents of the prescription, whether a prescription transfer is needed, and whether a prescription refill is needed) is determined. A prescription transfer is performed (if needed), but in any case, the prescription is fulfilled. The present approaches are performed seamlessly; that is, once the customer uploads or supplies the required images, prescription fulfillment (including transfers from other retailers or pharmacies) is automatic and does not require further customer interaction.

In aspects, these concepts relate to a system that automatically processes and orders medical prescriptions. The system allows customers to scan (e.g., using the camera of their phone) their retailer membership card, insurance card, payment method and any prescription. The prescription scanned may be a label, receipt or package, such as a bottle or box having the label affixed. Other examples are possible. Machine vision is used to extract the relevant information and is input into the system. This prevents tedious/time-consuming/error-prone manual entry of information by the user or an employee at a pharmacy. The scanned images (or video) are then sent to a server that uses a trained machine learning model to automatically determine if the prescription is a new prescription, a refill prescription or a prescription to be transferred from another pharmacy to the current pharmacy (i.e., a prescription not currently belonging to the current pharmacy). In order to determine that the prescription is a transfer prescription, the machine learning model is trained using examples of text, logos, colors, characters and other printed indicators on the prescription that indicate that the prescription is from or related to a competing pharmacy.

In other examples, an application is running on a customer's smartphone that prompts the customer to use the phone camera to capture images of the customer's cards and prescription. The captured images are transferred to a cloud-based server for processing. These approaches could also be implemented on a website or in-store kiosk. For a website implementation, the customer would need to upload captured images. For kiosk implementation, the kiosk would include an image capture device.

It will be appreciated that there are several approaches to scan customer information. First, in a "Scan as You Go" approach, in step-by-step fashion, the customer navigates to each of the membership card, insurance card, payment method and prescription sections of the interface and takes an image of the relevant card or prescription. The images are sent to the cloud server. Second, in "Scan All in One Go", in one step, the customer is prompted to capture an image of each of the membership card, insurance card, payment method and prescription in any order without having to select the prompts for each one. The images are sent to the cloud server. Third, in "Scan From a Video", the customer captures a video of the cards and prescription. The video is sent to the cloud server which extracts the relevant frames for processing. In some cases, it may not be necessary to scan one or more of the customer's payment method, membership card or insurance card if such information is already associated with the customer's account.

When the cloud server determines the appropriate prescription, the pharmacy backend service is used to automatically fill or refill the prescription, or to transfer the prescription to the current pharmacy and fill the prescription for the customer.

In many of these embodiments, a system includes a mobile electronic device, an electronic network, an electronic database, and a control circuit. The mobile electronic device is operated by a user and includes a sensor. The sensor is configured to obtain images of prescription items. The prescription items relate to or describe a medical prescription associated the user. The medical prescription is desired by the user to be serviced at a first pharmacy.

The electronic database includes a mathematical model. The control circuit is coupled to the electronic network and the electronic database.

The control circuit is configured to train the mathematical model to recognize prescription information by applying training images to the model. The control circuit is additionally configured to, subsequent to training the mathematical model, apply the images obtained from the mobile electronic device to the trained model and responsively receive prescription information. The prescription information indicates the contents of the prescription, whether a prescription transfer is needed, and whether a prescription refill is needed. The control circuit is further configured to determine an action based upon an analysis of the prescription information.

The action is taken to electronically instruct a human or robot to fulfill the prescription, and the action includes a human or robot retrieving medication from a storage area to fulfill the prescription. The action includes, when a prescription transfer is needed, transmitting an electronic message to a second pharmacy currently holding the medical prescription of the user.

In examples, the images are a series of images of different items, a single image with multiple items, or a video. Other examples are possible.

In other aspects, the model is a convolutional neural network. Other examples are possible.

In still other examples, the prescription items are an insurance card, a membership card, or a prescription. Other examples are possible.

In yet other aspects, the electronic message includes transfer instructions to the second pharmacy to transfer the prescription. In other aspects, a computer application program on the mobile electronic device presents to the user an option as to which type of items to scan.

In still other examples, the mobile electronic device is a smart phone, a tablet, a cellular phone, a laptop computer, or a personal computer. Other examples are possible.

In others of these embodiments, a mobile electronic device operated by a user is provided. The mobile electronic device includes a sensor and the sensor is configured to obtain images of prescription items. The prescription items relate to or describe a medical prescription associated the user. The medical prescription is desired by the user to be serviced at a first pharmacy.

An electronic network and an electronic database are also provided. The electronic database includes a mathematical model.

A control circuit is also provided. The control circuit is coupled to the electronic network and the electronic database.

The control circuit trains the mathematical model to recognize prescription information by applying training images to the model.

Subsequent to training the mathematical model, the control circuit applies the images obtained from the mobile electronic device to the trained model and responsively receiving prescription information. The prescription information indicates contents of the prescription, whether a prescription transfer is needed, and whether a prescription refill is needed.

The control circuit determines an action based upon an analysis of the prescription information. The action is taken to electronically instruct a human or robot to fulfill the prescription, and the action includes a human or robot retrieving medication from a storage area to fulfill the prescription. The action includes, when a prescription transfer is needed, transmitting an electronic message to a second pharmacy currently holding the medical prescription of the user.

Figure 1:
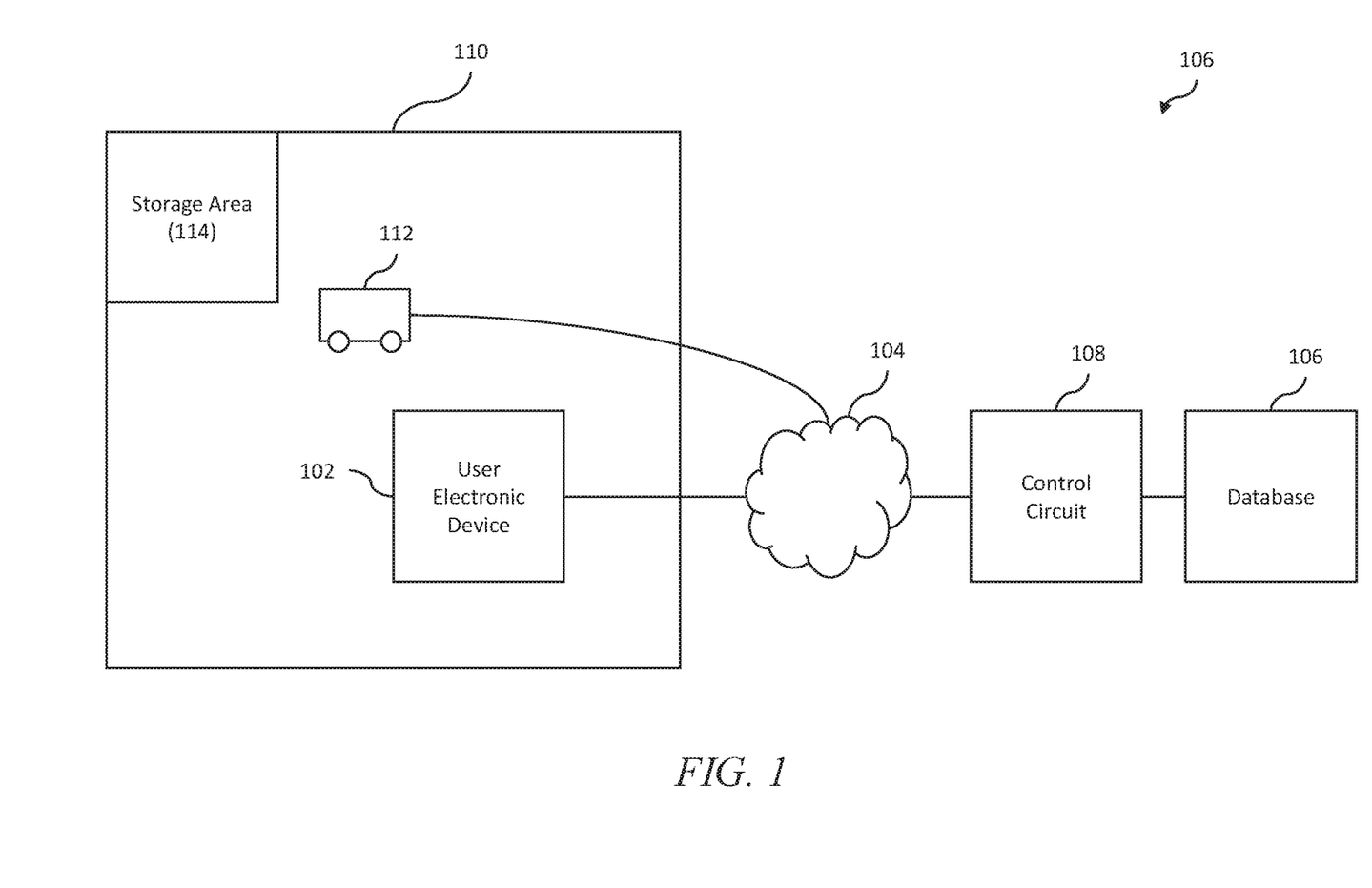
FIG. 1 comprises a diagram of a system as configured in accordance with various embodiments of these teachings.

Referring now to FIG. 1, a system 100 for fulfilling prescriptions is described. The system 100 includes a mobile electronic device 102, an electronic network 104, an electronic database 106, and a control circuit 108. A user may be operating the mobile electronic device 102 at a retail store 110. The retail store 110 may be any type of retail store and, in one example, may be a members-only store where access to the store is restricted to customers who have subscribed to membership in that store. The electronic network 104 may be any type of electronic network such as the internet, a wireless network, a cellular network, a local network, a wide area network, or any combination of these or other networks.

In examples, the mobile electronic device 102 is a smart phone, a tablet, a cellular phone, a laptop computer, or a personal computer. Other examples are possible. Many of the examples described herein are made in terms of the user with their user electronic device 102, being in or near the retail store 110. However, the user electronic device 102 may be at any location (e.g., at the home of the customer, at work, or in a doctor's office) and these same approaches may be utilized.

The mobile electronic device 102 is operated by a user and includes a sensor. In examples, the sensor is a camera or a scanner. Other examples of sensors are possible. The sensor is configured to obtain images of prescription items. The prescription items relate to or describe a medical prescription associated the user. In examples, the prescription items are an insurance card, a membership card for a customer at a retail store or chain of retail stores, or a prescription (e.g., a paper prescription, a label from a bottle that includes prescription information, a barcode to mention a few examples). Other examples are possible. The medical prescription is desired by the user to be serviced at a first pharmacy, for example, located in the store 110.

In one example, a computer software application may be executed at the mobile electronic device 102 that asks the user whether they wish to have their prescription serviced at a particular retail store or group of retail stores (e.g., at the retail store 110). Once the decision has been made to have their prescription serviced at the store 110, a series of screens may ask the user to select a method approach to scan in images, a delivery method, or to provide other instructions or information.

Various sequences of screens may be presented to the user once the customer selects an approach to enter information. For instance, in a "Scan as You Go" approach, in step-by-step fashion, the customer navigates to each of the membership card, insurance card, payment method and prescription sections of the interface and takes an image of the relevant card or prescription. In another example and in a "Scan All in One Go" approach, in one step, the customer is prompted to capture an image of each of the membership card, insurance card, payment method and prescription in any order without having to select the prompts for each one. In yet another example and in "Scan From a Video" approach, the customer captures a video of the cards and prescription. The video sent to the cloud server which extracts the relevant frames from the video for processing.

The electronic database 106 includes a mathematical model. In one example, the model is a convolutional neural network (CNN). Other examples are possible. When the model is a CNN model, different layers, tables, and/or other supporting structures are used to construct the model.

The control circuit 108 is coupled to the electronic network and the electronic database. It will be appreciated that as used herein the term "control circuit" refers broadly to any microcontroller, computer, or processor-based device with processor, memory, and programmable input/output peripherals, which is generally designed to govern the operation of other components and devices. It is further understood to include common accompanying accessory devices, including memory, transceivers for communication with other components and devices, etc. These architectural options are well known and understood in the art and require no further description here. The control circuit 108 may be configured (for example, by using corresponding programming stored in a memory as will be well understood by those skilled in the art) to carry out one or more of the steps, actions, and/or functions described herein.

The control circuit 108 may be disposed at various locations. In one example, the control circuit is disposed at a central processing location (e.g., headquarters). In other examples, the control circuit 108 is disposed at the retail store 110. The control circuit 108 may be disposed at multiple locations as well.

The control circuit 108 is configured to train the mathematical model to recognize prescription information by applying training images to the model. In these regards, training images are applied to the model and the physical characteristics of the model are changed as the model is trained. For example, when the model is a CNN model, then neural layers and the structure of these layers is altered from a first structure or state to a second structure or state.

The control circuit 108 is additionally configured to, subsequent to training the mathematical model, apply the images obtained from the mobile electronic device 102 to the trained model and responsively receive prescription information. The prescription information indicates the contents of the prescription, whether a prescription transfer is needed, and whether a prescription refill is needed.

The control circuit 108 is further configured to determine an action based upon an analysis of the prescription information. For example, analysis of the information received from the model may indicate the contents (e.g., medication and medication dosages) of the prescription, and the present supplier of the prescription. Control logic may be used to determine whether a transfer is needed. For example, the control logic may determine whether the current provider of the prescription (indicated in the images) is the same as the desired provider of the prescription (e.g., indicated by a user entering this information at the user electronic device 102). In this case, the action to take is to cause a transfer of the prescription.

In aspects, the action is taken to electronically instruct a human or robot 112 (e.g., an automated vehicle such as an automated ground vehicle or aerial drone) to fulfill the prescription. In examples, the action includes a human or robot 112 retrieving medication from a storage area 114 to fulfill the prescription. It will be appreciated that in obtaining the prescription the robot 112 may independently navigate through the store 110 and/or through storage areas in the store. The robot 112 may include levers, grips, arms, suction grips, and other mechanical features that allow the robot to retrieve the medical prescriptions from shelves. In some examples, the prescriptions may be in pre-packaged containers while in other examples, the prescriptions must be sorted (e.g., a determined dosage of pills must be moved from a larger storage container into a container that is actually given to the customer). When the prescription is sorted, this may be performed by one or more robots, humans, or some combination of robots and humans. In any case, it will be understood that the movement and/or actions of the robots and/or humans represent a physical interaction of the robots and/or humans with the retail store 1110 and/or items and fixtures (e.g., shelves) in the retail store 110. Navigation may be made so as to avoid collisions with humans or objects.

In other aspects, the action includes, when a prescription transfer is needed, transmitting an electronic message to a second pharmacy currently holding the medical prescription of the user.

Figure 2:
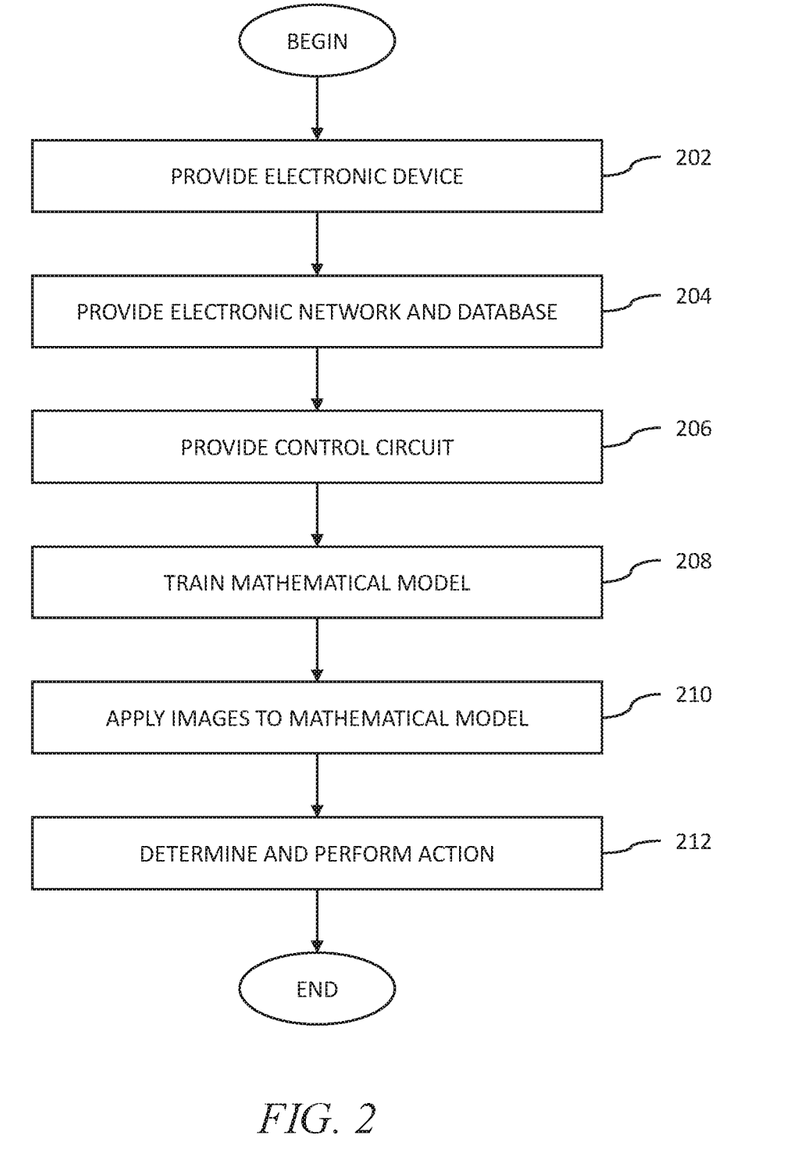
FIG. 2 comprises a flowchart as configured in accordance with various embodiments of these teachings.

Referring now to FIG. 2, one example of an approach for fulfillment of prescriptions is described. At step 202, a mobile electronic device operated by a user is provided. The mobile electronic device includes a sensor and the sensor is configured to obtain images of prescription items. In one example, the mobile device is a smartphone with a camera that can be used to obtain the images. The prescription items relate to or describe a medical prescription associated the user. In one example, a paper prescription (e.g., label or labels from medication bottles), an insurance card, and a membership card of a particular retailer may be the prescription items that are scanned. The medical prescription is desired by the user to be serviced at a first pharmacy.

At step 204, an electronic network and an electronic database are also provided. The electronic database includes a mathematical model. In examples, the CNN model with various physical layers. Other examples of models are possible.

At step 206, a control circuit is also provided. The control circuit is or has been coupled to the electronic network and the electronic database.

At step 208, the control circuit trains the mathematical model to recognize prescription information by applying training images to the model. In aspects, training images are applied to the model to recognize features such as words, logos of different retailers (e.g., the retailer where the prescription is located, which may be a competitor of the retailer where the customer desires the prescription to be fulfilled). The overall goal is to, once training is a complete, apply images to the trained model. For example, applying an image of an insurance card having a logo (e.g., symbol) relating to Insurance Provider A to the trained model produces a result (from the model) that the card belongs to Insurance Provider A. In another example, applying an image of a prescription having a logo (e.g., symbol) relating to Retailer B to the trained model produces a result (from the model) that the prescription is currently being serviced by Retailer B. In yet another example, applying an image of a retail store membership card having a logo (e.g., symbol) relating to Retailer C to the trained model produces a result (from the model) that the card belongs to Retailer C and, if the customer's name and membership number are on the card (and if this can be later verified), the customer is a verified member of Retailer C.

It will be appreciated that training occurs prior to applying the customer-obtained images to a trained model. In other words, first the model is trained and then the trained model is used. Once trained, the model may be final in that it is not trained again. In other examples, the trained model itself may be periodically fine-tuned to improve its performance.

At step 210 and subsequent to training the mathematical model, the control circuit applies the images obtained from the mobile electronic device to the trained model and responsively receives prescription information from the trained model. The prescription information indicates contents of the prescription, whether a prescription transfer is needed, and whether a prescription refill is needed. As mentioned, the model produces results when images are applied to the model that includes the prescription information.

At step 212, the control circuit determines an action based upon an analysis of the prescription information. The action is taken to electronically instruct a human or robot to fulfill the prescription, and the action includes a human or robot retrieving medication from a storage area to fulfill the prescription. The action includes, when a prescription transfer is needed, transmitting an electronic message to a second pharmacy currently holding the medical prescription of the user.

As described herein, various control logic can be used to determine the action or actions to take. The control logic may also verify that the customer is a member of a retail store and is allowed to obtain the prescription at the store. The control logic may also determine that a transfer is needed (the present pharmacy servicing the prescription is different from the desired pharmacy to service the prescription as indicated by the customer).

Figure 3:
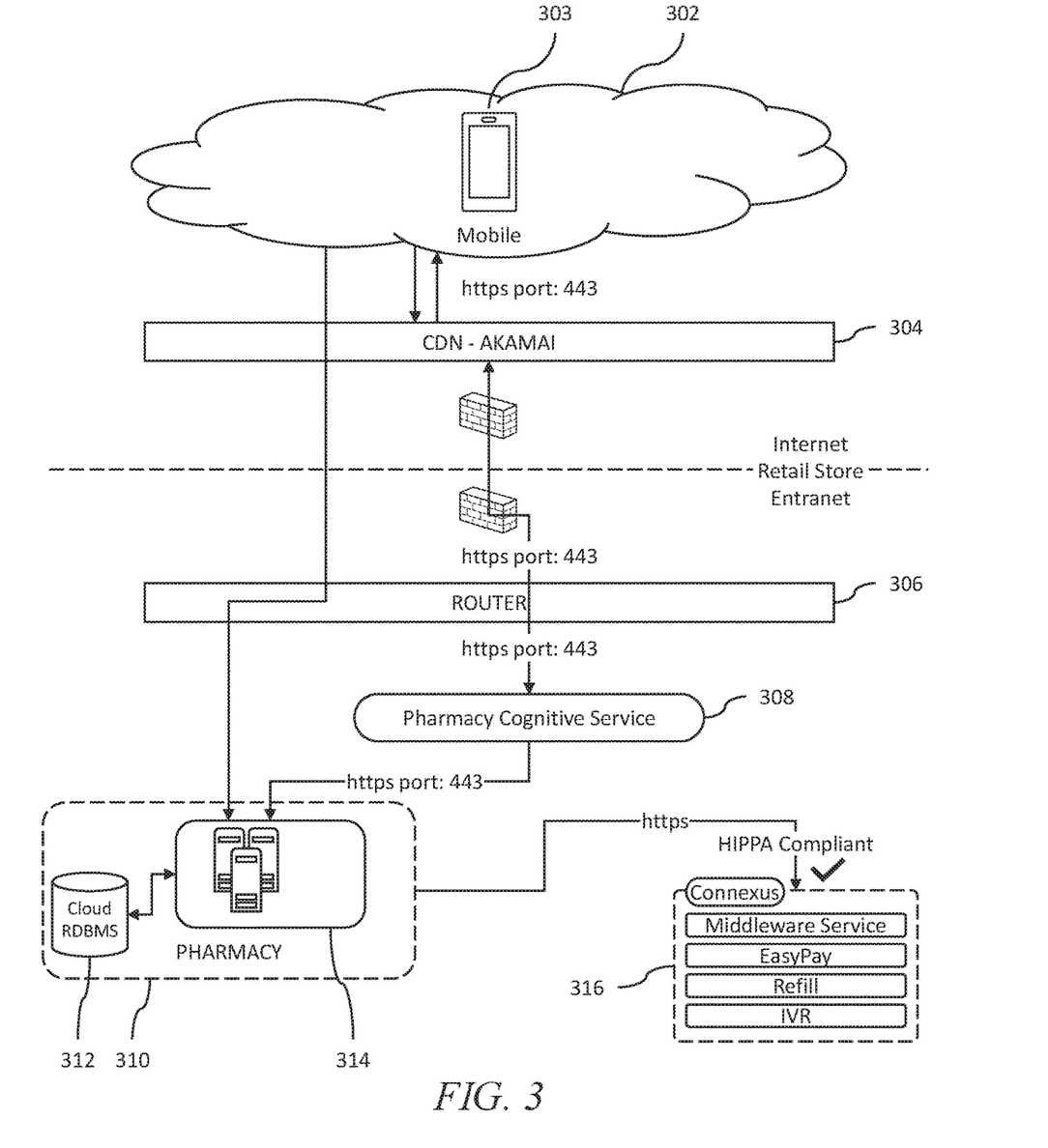
FIG. 3 comprises a diagram of a system as configured in accordance with various embodiments of these teachings.

Referring now to FIG. 3, one example of a system 300 for fulfilling prescriptions is described. The system 300 includes a network 302 (including a mobile wireless device 303), a content delivery engine (CDN) 304, a routing service 306, a cognitive service 308, a pharmacy service 310 (including a database 312 and core logic 314), and a patient data service 316. It will be appreciated that these elements may be implemented as any combination of electronic hardware and computer software elements. These elements can take a variety of forms such as computer processors, gateways, memories, computer instructions, or servers to mention a few examples.

The network 302 is any type of electronic network such as the internet. The CDN 304 stores and delivers images near to the user. The router 306 provides the routing capabilities across different URLs and allows selective exposure of resources.

The Cognitive Service 308 has three different components: a model, a training component, and a feedback component.

The model component extracts the data out of an image with a certain confidence score. The model is responsible for analyzing various images and categorizing it as a credit card, membership card and/or prescription information. Once initial categorization is done, then it relies upon optical character recognition (OCR) to extract the text out of the image. After the text extraction, various machine learning models are used to determine the meaning of a text. Depending upon the confidence score, a decision is made as whether to rely upon the outcome. All the images which have a low score output are moved to the feedback component.

The training component is responsible for training of different models for pharmacy. Initial training is performed across various credit/health savings account (HSA)/prescriptions to identify which kind of data is being processed. Different models trained to extract text from the images and then to categorize the text into a certain category (e.g., patient name, medicine name, club address, phone number). The models are tuned based on various inputs and training is run on a need basis (i.e., as needed). Once training is complete, the model component is replaced with the output from the training data.

The feedback component is responsible for making the machine learning algorithm better and accurate. Any data which comes with a low confidence score, a manual analysis is performed to determine the ideal output from the data. Based on the need, the machine learning model is tuned, so that it can handle images with different kind of features. Sometimes, the data is discarded as an outlier. Once a new model is created, the new model is trained and then it is ensured it provides accurate output for the older set of data. This kind of continuous feedback makes the system better, more accurate, and more robust.

The pharmacy service 310 includes a database 312 and core logic 314. In aspects, the pharmacy service 310 is a Java-based system, which is responsible for maintaining the overall state of pharmacy orders. This contains the core logic 314 to communicate with other retail store systems and the patient data service 318. The sanity of any pharmacy order is maintained by pharmacy service 310. The state of each order is also maintained in the database 312 and a distributed cache to overcome latency issues.

The patient data service 316 is the source of truth for all patient data. The service 316 (implemented as any combination of hardware or software) contains all the medicine history and patient information for customers (e.g., customers of the pharmacy) and tracks the retail-side delivery of orders. In aspects, all the orders details are updated in patient data service 316. The patient data service 316 may comply with Health Insurance Portability and Accountability Act (HIPAA).

Figure 4:
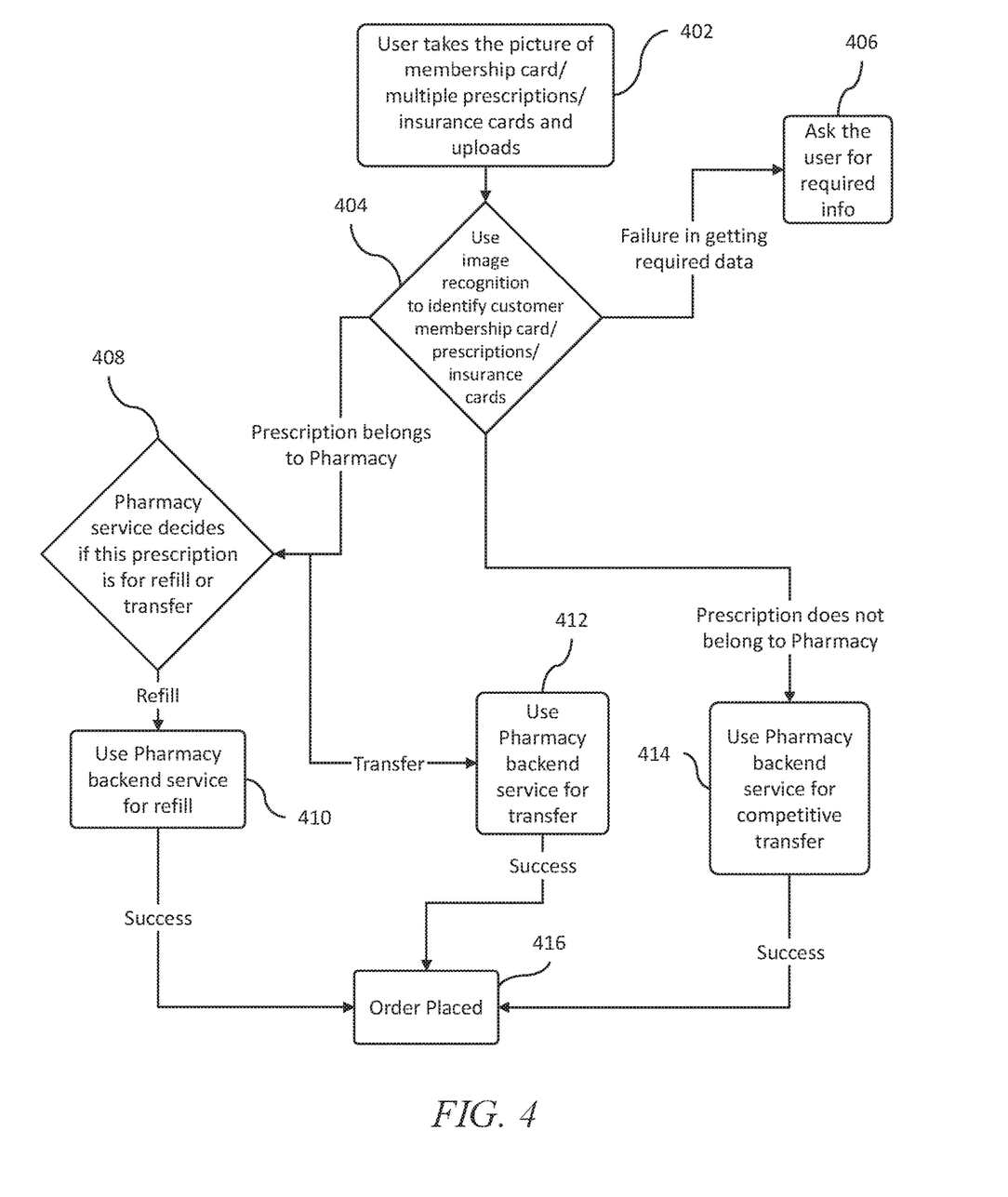
FIG. 4 comprises a flowchart as configured in accordance with various embodiments of these teachings.
Figure 5:
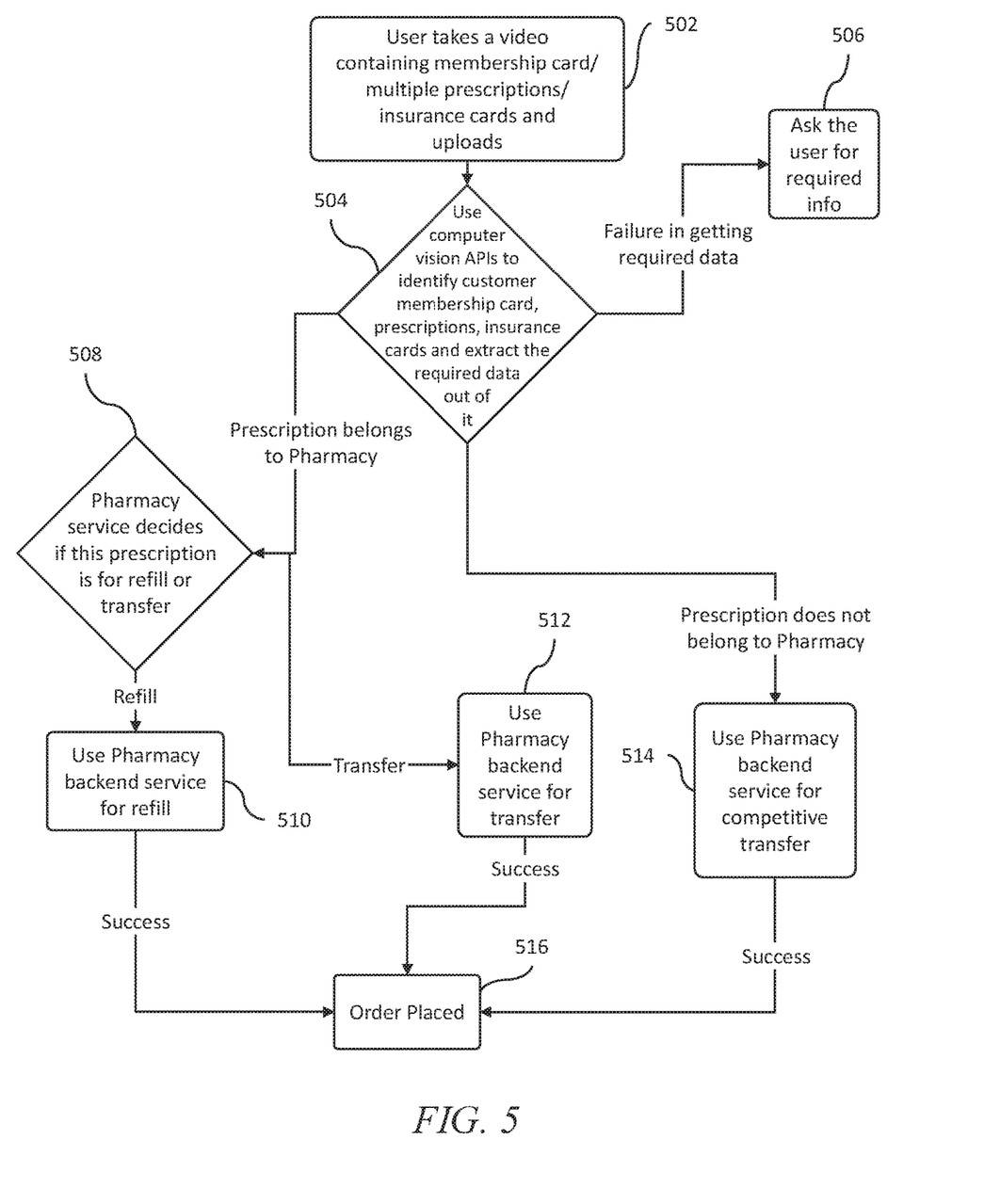
FIG. 5 comprises a flowchart as configured in accordance with various embodiments of these teachings.
Figure 6:
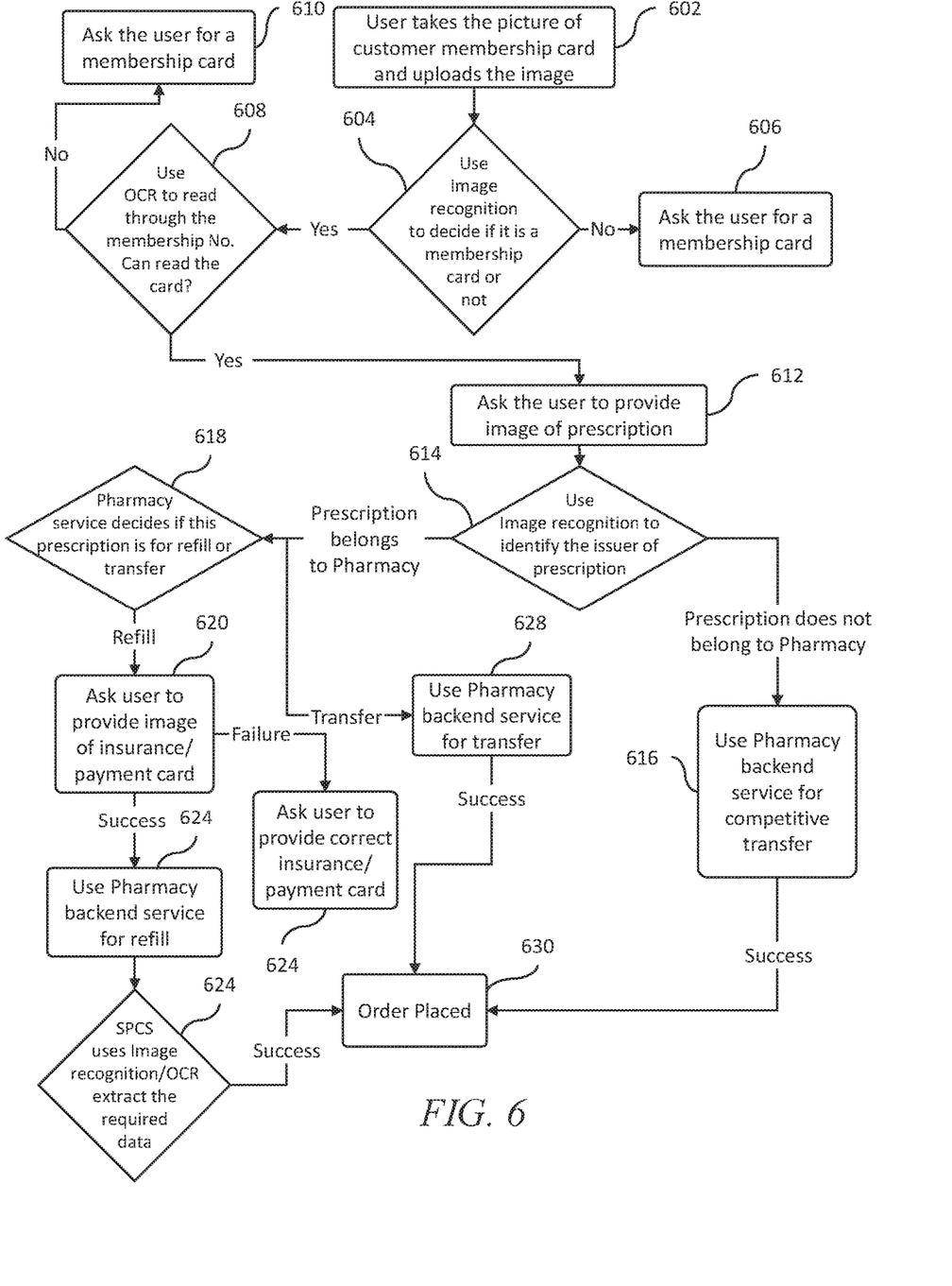
FIG. 6 comprises a flowchart as configured in accordance with various embodiments of these teachings.

In the examples of FIGS. 4-6, a prescription is to be processed by a retail store. In this case, the retail store (e.g., Sam's Club), is a members-only store and the customer has a membership card. The member also has an insurance card (showing, for example, the insurance carrier, and an insurance policy number), and prescription information (e.g., a paper prescription listing the medical prescriptions by, for instance, name and amount). These approaches result in an order being placed. Placement of an order, in aspects, may include electronically ordering medication from a supplier, having a robot physically retrieve the medication from a shelf (and/or package the medication in appropriate container(s)), and/or send electronic messages to customers (or store employees). Other examples are possible.

Referring now to FIG. 4, one example of an approach for fulfilling a prescription is described. At step 402, the user takes a single photo (e.g., with the camera on their user electronic device) and the photo includes their membership card, their prescription/insurance card, and their prescription. In other aspects, multiple photos (electronic images) may be obtained (e.g., each object may be photographed separately).

At step 404, the system uses image recognition approaches to identify the membership card, the insurance card, and the prescriptions. These approaches may, in one example, use OCR approaches and CNN models to obtain information such as membership information and status of the customer, the retail chain that has (is currently serving or responsible for) the prescription, the store within the chain that has the prescription, whether another store from another chain has the prescription, insurance information concerning the prescription, and details concerning the prescription itself (e.g., medications, dosages, amounts and so forth).

If at step 404, there is a failure to get required data (e.g., the user fails to provide a membership card), at step 406 the user is asked for the required information.

If at step 404, the prescription is determined not to belong to the retail store the customer is located and desires to have the prescription filled (the customer is in a Sam's Club store, but the prescription is held by another retail store X), then at step 414 the store's (e.g., Sam's Club) back-end computer system executes a competitive transfer (e.g., this may involve exchanging electronic messages with store X informing store X that the prescription is being transferred to Sam's Club). If this step is successful, an order is placed at step 416.

If at step 404, the prescription belongs to the retail store the customer is located and desires to have the prescription filled (e.g., the customer is in a Sam's Club store and desires the prescription to be filled by Sam's Club), then at step 408, the system determines if the prescription is for a refill or a transfer.

If the answer at step 408, is refill, then at step 410, the backend computer system of the pharmacy is used to perform the refill. If this step is successful, an order is placed at step 416.

If the answer at step 408 is transfer, at step 412 the user backend service is used to perform a transfer. In this case, the transfer is within the same retail chain (e.g., from one Sam's Club to another Sam's Club). If this step is successful, an order is placed at step 416.

Referring now to FIG. 5, another example of an approach for fulfilling a prescription is described.

At step 502, the user takes a video (e.g., with the camera on their user electronic device) and the video includes their membership card, their prescription/insurance card, and their prescription.

At step 504, the system uses image recognition approaches to identify the membership card, the insurance card, and the prescriptions. These approaches may, in one example, use OCR approaches and CNN models to obtain information such as membership information and status of the customer, the retail chain that has (is currently serving or responsible for) the prescription, the store within the chain that has the prescription, whether another store from another chain has the prescription, insurance information concerning the prescription, and details concerning the prescription itself (e.g., medications, dosages, amounts and so forth).

If at step 504, there is a failure to get required data (e.g., the user fails to provide a membership card), at step 506 the user is asked for the required information.

If at step 504, the prescription is determined not to belong to the retail store the customer is located and desires to have the prescription filled (the customer is in a Sam's Club store, but the prescription is held by another retail store X), then at step 514 the store's (e.g., Sam's Club) back-end computer system executes a competitive transfer (e.g., this may involve exchanging electronic messages with store X informing store X that the prescription is being transferred to Sam's Club). If this step is successful, an order is placed at step 516.

If at step 504, the prescription belongs to the retail store the customer is located and desires to have the prescription filled (e.g., the customer is in a Sam's Club store and desires the prescription to be filled by Sam's Club), then at step 408, the system determines if the prescription is for a refill or a transfer.

If the answer at step 508 is refill, then at step 510, the backend system of the pharmacy is used to perform the refill. If this step is successful, an order is placed at step 516.

If the answer at step 508 is transfer, at step 512 the user backend service is used to perform a transfer. In this case, the transfer is within the same retail chain (e.g., from one Sam's Club to another Sam's Club). If this step is successful, an order is placed at step 516.

Referring now to FIG. 6, another example of an approach for fulfilling a prescription is described.

At step 602, the user takes a photo of their membership card (e.g., with the camera on their user electronic device) and uploads the image for processing.

At step 604, the system determines (using image recognition) whether the membership card is from the retail (e.g., when the customer is in Sam's Club and desires the prescription to be fulfilled by Sam's Club, is the membership card from Sam's Club). If the answer is negative, then at step 606 the system asks the customer to supply the correct card. If the answer is affirmative, step 608 is executed.

At step 608, OCR approaches are used to determine the membership number. If this cannot be obtained, step 610 is executed where the system asks the customer for a membership card from the retailer. If the number can be obtained or determined, at step 612 the customer is asked to provide an image of the prescription.

At step 614, the system uses image recognition approaches to identify the issuer (holder) of the prescription. If the holder is not the same as the store where the customer desires the prescription to be fulfilled, step 616 is executed. For example, the customer is in a Sam's Club store, but the prescription is being issued by another retail store X. At step 616 the store's (e.g., Sam's Club) back-end computer system executes a competitive transfer (e.g., this may involve exchanging electronic messages with store X informing store X that the prescription is being transferred to Sam's Club). If this step is successful, an order is placed at step 630.

If step 614 determines the prescription belongs to the retailer (e.g., the customer is in a Sam's Club store and the prescription is being issued by Sam's Club), then step 618 is executed. At step 618, the store's back end system determines if the prescription is a refill or a transfer. If the answer at step 618 is transfer, step 628 is executed. At step 628, the pharmacy back end system transfers the prescription from two stores in the same retail chain (e.g., between two Sam's Club stores). If this step is successful, an order is placed at step 630.

If the answer at step 618 is that the prescription is a refill, then at step 620 the system asks the customer to provide an image of the insurance or payment card. If there is a failure with this step, at step 622 the system asks the user to provide the correct insurance or payment card. If step 620 is successful, then at step 624 the backend pharmacy service is used to obtain the refill. At step 626, the system uses the OCT and/or image recognition to extract the relevant prescription data (e.g., medication and amounts of medication). Next, an order is placed at step 630.

Figure 7:
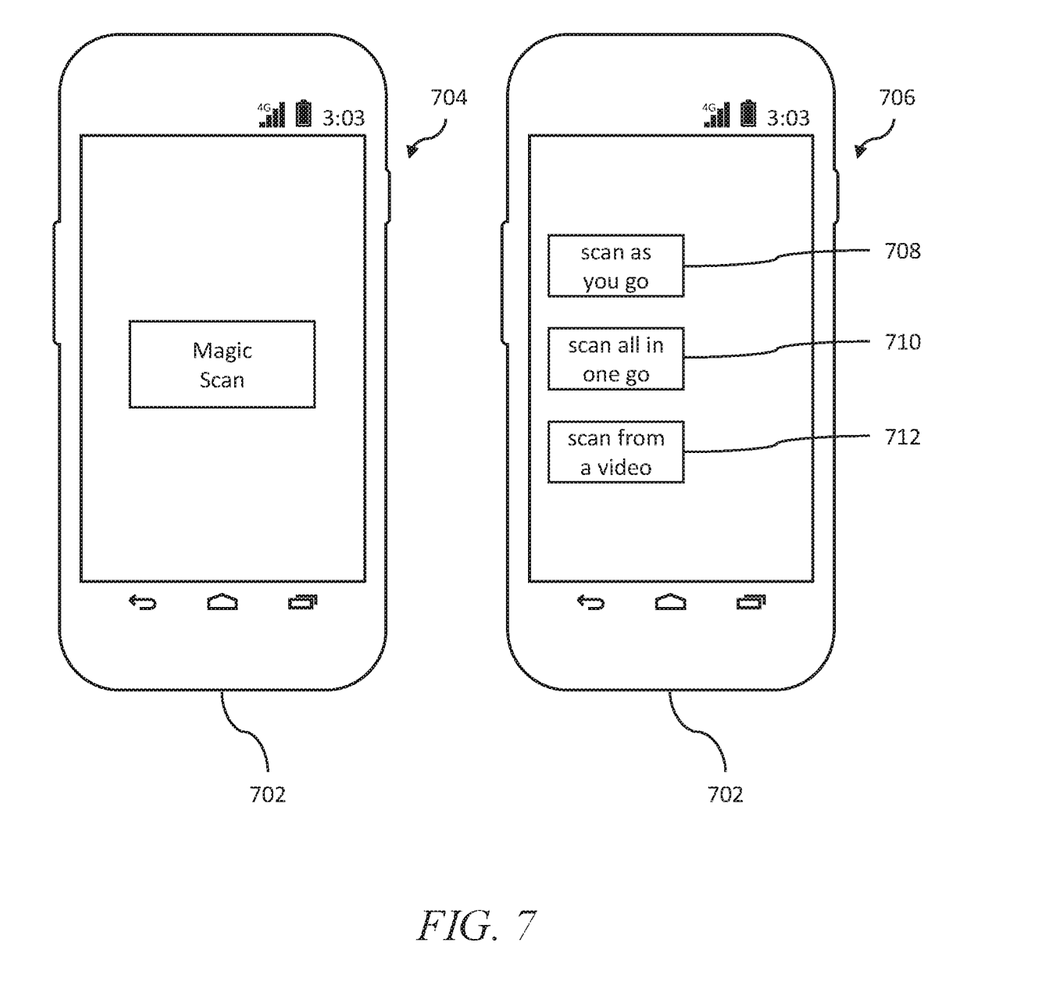
FIG. 7 comprises a diagram of a system as configured in accordance with various embodiments of these teachings.

Referring now to FIG. 7, one example of an approach for fulfilling a prescription is described. A user electronic device 702 includes a first screen 704 and a second screen 706. The first screen 702 announces the service and allows the user (e.g., by selecting the service) to utilize the service (e.g., in this case, the service may be called "Magic Scan").

The second screen 706 includes icons 708 (to select "scan-as-you-go"), 710 (to select "scan all in one go"), and 712 (to select "Scan From a Video"). Once one of these icons is selected by the user, the user device 702 may be configured or arranged to perform the particular service selected (e.g., if "Scan From a Video" is selected, a camera on the device 702 is initialized to record video).

As explain elsewhere, herein the "Scan-as-You-Go" service is where the user takes the image of the membership card, then the insurance or prescription card. The "scan all in one go" service allows the user uploads all images in one action. The images are analyzed and placed in order. The user can provide multiple prescriptions. The "Scan From a Video" service allows a user to prepare a video with membership card and prescription or insurance card. The images are analyzed and the order is placed.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A system, comprising:
an electronic network;
an electronic database, the electronic database including a mathematical model;
a control circuit, the control circuit coupled to the electronic network and the electronic database, the control circuit being configured to:
train the mathematical model to recognize prescription information by applying training images to the model;
wherein the training extracts data from training images with a confidence score, and the confidence score determines whether to rely on the training images for the training, fine-tune the model subsequent to training, and/or to discard selected ones of the training images and wherein the training images contain images of insurance cards, membership cards, and prescriptions;
wherein the membership cards and prescriptions include indicia that the membership cards and prescriptions are from or are related to competing pharmacies that are different from an existing pharmacy currently fulfilling medical prescriptions for a user;
wherein the mathematical model is a neural network comprising a structure including neural layers, and the neural layers are changed from a first structure or a first state to a second structure or a second state because of the training such that the second structure or state is automatically configured to recognize and discern information from the images of the insurance cards, membership cards and prescriptions when applied to the neural network, and the first structure or state is unable to recognize and discern information from the images of the insurance cards, membership cards, and prescriptions;
wherein subsequent to the training:
a transaction to fulfill and potentially transfer an existing prescription of the user from the existing pharmacy to a pharmacy associated with a store in which the user is currently located is initiated by a camera on a mobile electronic device of the user being actuated to obtain one or more images, the existing prescription previously having been serviced by the existing pharmacy, the one or more images including images of an existing medical prescription of the user, an existing membership card of the user, the existing membership card relating to or identifying the store the user is currently located, and/or an insurance card of the user, the mobile electronic device transmitting the one or more images to the control circuit via the electronic network after obtaining the images;
the control circuit receives the one or more images via the electronic network while the user is in a store;
the control circuit applies the one or more images obtained from the mobile electronic device to the trained model and automatically and responsively receives from the trained model prescription information, the prescription information indicating contents of the prescription, whether a prescription transfer is needed and, if needed an identity of the existing pharmacy, and whether a prescription refill is needed;
the control circuit determines an action based upon an analysis of the prescription information; and
based on the determined action the control circuit electronically controls a robot to retrieve medication from a storage area to fulfill the prescription;
wherein the action includes, when a prescription transfer is needed, transmitting an electronic message to the existing pharmacy currently holding the medical prescription of the user to transfer the existing medical prescription to the pharmacy of the store in which the user is currently located and the existing medical prescription is subsequently electronically transferred to the pharmacy of the store where the user is currently located.

2. The system of claim 1, wherein the one or more images are a series of images of different items, a single image with multiple items, or a video.

3. The system of claim 1, wherein the model is a convolutional neural network.

4. The system of claim 1, wherein a computer application program on the mobile electronic device presents to the user an option as to which type of items to scan.

5. The system of claim 1, wherein the mobile electronic device is a smart phone, a tablet, a cellular phone, a laptop computer, or a personal computer.

6. A method, comprising:
training, by a control circuit via an electronic network, a mathematical model to recognize prescription information by applying training images to the mathematical model, the mathematical model implemented on an electronic database coupled to the electronic network;
wherein the training by the control circuit includes extracting data from training images with a confidence score, wherein the confidence score is used by the control circuit to determine whether to rely on the training images for the training, fine-tune the mathematical model subsequent to the training, and/or to discard selected ones of the training images, and wherein the training images contain images of insurance cards, membership cards, and prescriptions;
wherein the membership cards and the prescriptions include indicia that the membership cards and the prescriptions are from or are related to competing pharmacies that are different from an existing pharmacy currently fulfilling medical prescriptions for a user;
wherein the mathematical model is a neural network comprising a structure including neural layers, and the neural layers are changed from a first structure or a first state to a second structure or a second state because of the training such that the second structure or state is automatically configured to recognize and discern information from the images of the insurance cards, the membership cards and the prescriptions when applied to the neural network, and the first structure or state is unable to recognize and discern information from the images of the insurance cards, the membership cards, and the prescriptions;

initiating, by the control circuit via the electronic network, a transaction to fulfill and potentially transfer an existing prescription of the user from the existing pharmacy to a pharmacy associated with a store in which user is currently located based on a camera on a mobile electronic device of the user being actuated to obtain one or more images, the existing prescription previously having been serviced by the existing pharmacy, the one or more images obtained including images of an existing medical prescription of the user, an existing membership card of the user, the existing membership card relating to or identifying the store in which the user is currently located, and/or an insurance card of the user;

receiving, by the control circuit via the electronic network, the one or more images obtained from the mobile electronic device while the user is in the store;

applying, by the control circuit, the one or more images obtained from the mobile electronic device to the trained model;

responsive to applying the one or more images obtained to the trained model, automatically receiving from the trained model prescription information, the prescription information indicating contents of the prescription, whether a prescription transfer is needed, whether a prescription refill is needed and an identity of the existing pharmacy;

analyzing, by the control circuit, the prescription information received from the trained model;

determining, by the control circuit, an action based upon an analysis of the prescription information; and based on the determined action, electronically controlling, by the control circuit, a robot to retrieve medication from a storage area to fulfill the prescription;

wherein the action includes, when a prescription transfer is needed, transmitting an electronic message to the existing pharmacy currently holding the medical prescription of the user to transfer the existing medical prescription of the user to the pharmacy of the store in which the user is currently located and the existing medical prescription of the user is subsequently electronically transferred to the pharmacy of the store where the user is currently located.

7. The method of claim 6, wherein the one or more images are a series of images of different items, a single image with multiple items, or a video.

8. The method of claim 6, wherein the model is a convolutional neural network.

9. The method of claim 6, wherein a computer application program on the mobile electronic device presents to the user an option as to which type of items to scan.

10. The method of claim 6, wherein the mobile electronic device is a smart phone, a tablet, a cellular phone, a laptop computer, or a personal computer.

11. A device, comprising:
a control circuit, the control circuit coupled to an electronic network and an electronic database, the control circuit being configured to:
train a model implemented on the electronic database to recognize prescription information by applying training images to the model, wherein the training extracts data from training images with a confidence score, using the confidence score to determine whether to rely on the training images for the training and to fine-tune the model subsequent to training, and wherein the training images contain images of insurance cards, membership cards, and prescriptions;
wherein the membership cards and the prescriptions include indicia that the membership cards and the prescriptions are related to competing pharmacies that are different from an existing pharmacy currently fulfilling medical prescriptions for a user;
an image capture device configured to obtain one or more images associated with a user in a location and transmit the one or more images to the control circuit while the user is in the location;
the control circuit receives the one or more images while the user is in the location and apply the one or more images to the trained model to automatically receivs from the trained model prescription information, the prescription information indicating contents of the prescription, whether a prescription transfer is needed and, if needed an identity of the existing pharmacy, and whether a prescription refill is needed;
the control circuit determines an action based upon an analysis of the prescription information; and
based on the determined action the control circuit electronically controls a robot to retrieve medication from a storage area to fulfill the prescription;
wherein the action includes, when a prescription transfer is needed, transmitting an electronic message to the existing pharmacy currently holding the medical prescription of the user to transfer the existing medical prescription to the pharmacy of the store in which the user is currently located and the existing medical prescription is subsequently electronically transferred to the pharmacy of the store where the user is currently located.

12. The device of claim 11, wherein the one or more images are a series of images of different items, a single image with multiple items, or a video.

13. The device of claim 11, wherein the model is a convolutional neural network.

14. The device of claim 11, wherein the device is an in-store kiosk.

15. The device of claim 11, wherein the device is a smart phone, a tablet, a cellular phone, a laptop computer, or a personal computer.

* * * * *